(12) United States Patent
Reader, Jr. et al.

(10) Patent No.: US 6,840,668 B1
(45) Date of Patent: Jan. 11, 2005

(54) THERMOGRAVIMETRICAL ANALYZER AUTOSAMPLER SEALED SAMPLE PAN

(75) Inventors: John R. Reader, Jr., Newark, DE (US); Amichai Shdaimah, Ardmore, PA (US); Fred L. Ferguson, Wilmington, DE (US)

(73) Assignee: Waters Investment Limited, New Castle, DE (US)

( * ) Notice: Subject to any disclaimer, the term of this patent is extended or adjusted under 35 U.S.C. 154(b) by 0 days.

(21) Appl. No.: 10/626,696

(22) Filed: Jul. 25, 2003

(51) Int. Cl.⁷ .................. G01N 25/20; G01N 35/10; G05B 19/04; B25J 15/00
(52) U.S. Cl. .................. 374/14; 422/51; 422/63; 422/64; 422/67; 422/102; 901/33; 901/38; 220/359.1
(58) Field of Search .................. 374/14, 12, 10, 374/31; 215/232, 258, 250, 253; 220/359.1, 267, 268, 276, 752, 760, 773; 422/51, 99, 102, 63–67, 100; 73/864.91, 863.11; 901/33, 38; 700/255; 318/568.22

(56) References Cited

U.S. PATENT DOCUMENTS

| | | | | |
|---|---|---|---|---|
| 2,847,663 A | * | 8/1958 | Stoddard | 901/38 |
| 3,285,053 A | * | 11/1966 | Mazieres | 374/13 |
| 3,929,251 A | * | 12/1975 | Urmston | 215/253 |
| 4,159,057 A | * | 6/1979 | Teramoto | 374/12 |
| 4,330,933 A | * | 5/1982 | Bullinger et al. | 374/12 |
| 4,801,429 A | * | 1/1989 | Torfs et al. | 374/12 |
| 4,874,250 A | * | 10/1989 | Gonner | 374/12 |
| 5,165,792 A | | 11/1992 | Crowe et al. | |
| 5,215,377 A | * | 6/1993 | Sugano | 374/14 |
| 5,306,087 A | * | 4/1994 | Nakamura et al. | 374/14 |
| 5,398,556 A | * | 3/1995 | Lang | 374/12 |
| 5,483,843 A | * | 1/1996 | Miller et al. | 422/63 |
| 6,468,475 B1 | * | 10/2002 | Goenner et al. | 422/64 |
| 2002/0053244 A1 | * | 5/2002 | Goenner et al. | 73/864 |

* cited by examiner

*Primary Examiner*—Diego Gutierrez
*Assistant Examiner*—Stanley J. Pruchnic, Jr.
(74) *Attorney, Agent, or Firm*—Shaw Pittman LLP

(57) ABSTRACT

The present invention relates to apparatus, systems, and methods for opening an autosampler sealed sample pan prior to TGA testing. The sealed sample pan comprises a pan, cover, and bail. A notch is formed in the seal sample pan cover. The cover can be opened by applying a concentrated force to the inside of the notch with a punch element integrated into the autosampler. This causes the center disk portion of the cover to be partially sheared and the sealed sample pan to be opened. It also prevents the punch element from touching the sample. A force sensor is used to determine if the cover has been opened. If the cover has been opened, then the sample pan is loaded to the TGA balance. If the cover has not been opened, the autosampler will not load the pan and will automatically move to the next sealed sample pan.

27 Claims, 11 Drawing Sheets

THERMOGRAVIMETRICAL ANALYZER AUTOSAMPLER SEALED SAMPLE PAN

BACKGROUND OF THE INVENTION

1. Field of the Invention

The present invention relates generally to sealed sample pans, which are used with an autosampler mounted on a thermogravimetrical analyzer (TGA). More particularly, the present invention relates to sealed sample pans designed to keep the sample isolated from the ambient environment until the beginning of an experiment.

2. Background Information

A TGA is an instrument for measuring the thermal stability of a sample. The instrument heats a sample and measures the weight gain or loss during the process. In a typical instrument, a sample is suspended from a very sensitive balance. When heated, the sample undergoes a physical change. The weight versus temperature and weight versus time is then recorded and plotted for each sample. TGAs are described, for example, in U.S. Pat. No. 5,165,792, which is incorporated by reference herein.

A TGA autosampler is an accessory that is used to automatically load samples into and unload samples from a TGA. It allows a TGA to be operated unattended for long periods of time. It typically contains a programmable tray capable of holding between 16 and 64 sample pans and a mechanism for moving these pans between the tray and the TGA.

A sealed sample pan is the enclosure containing the sample to be tested. It is designed so that it can be moved automatically by the autosampler from the tray, to the TGA, and back to the tray. A sample is hermetically sealed in a sealed sample pan before it is placed on the autosampler tray. However, just before being placed in the TGA, each sample must be exposed to the ambient environment. As a result, the sealed sample pan must be opened just prior to loading it into a TGA.

The current known method of opening a sealed sample pan consists of piercing the pan with a tapered pin just prior to loading. This method has a number of disadvantages. One, because the piercing element penetrates the sample pan, it can easily touch the sample during or after the penetration and may contaminate it or may contaminate the next sample. Two, the size of the pierced hole is not repeatable due to variables in the system and may result in inconsistent test results. Three, there are no means to determine whether or not the pan was pierced during the process. This is important, because if the sample pan is not pierced, the results of the measurement would not be valid. Also, some sealed sample pans must be opened to expose the sample to oxygen so that it can oxidize. Other samples generate gases during heating and will explode if not opened.

In view of the foregoing, a substantial need exists for a sealed sample pan and systems and methods of opening a sealed sample pan just prior to loading that prevent sample contamination or cross contamination with other samples, produce an opening of repeatable size, and provide a means to determine whether or not the pan was opened during the process.

BRIEF SUMMARY OF THE INVENTION

The present invention is a sealed sample pan and a system and method for keeping the sample isolated from the ambient environment until the beginning of a TGA experiment, and then automatically opening the sample pan and loading it to the balance without human intervention. In a preferred embodiment, the sealed sampled pan is comprised of three parts. These are (1) a pan in which the sample is placed, (2) a cover which is placed on the pan and sealed to it by means of a dedicated press tool, and (3) a bail which is constructed of, for example, formed wire or sheet metal, and designed to hold the pan and to provide the interface to the TGA balance hang-down hook. Depending on the desired application, the pan can be constructed from various materials including but not limited to aluminum, stainless steel, gold, and platinum. Typically, aluminum is used for all three parts.

The invention provides a means to open a section of the pan cover and expose the sample to the environment just before it is loaded into the balance. In a preferred embodiment, a notch is formed on the top flat surface of the cover. In preferred embodiments, the shape of the notch is circular. Alternative shapes such as a teardrop, oval, or polygon (e.g. triangle, rectangle, hexagon, etc.) may also be used. However, shapes other than circular may require that the sealed sample pan be aligned before it is opened. The thickness of the pan cover is reduced locally in the notch. The cover can be opened by applying a concentrated force to the inside of the circular notch, which is the weakest section of the cover, causing part of the center disk portion of the cover to be sheared downward from the rest of cover, outside the ring. As a result, part of the center disk portion of the cover is detached from the pan cover and part remains attached, creating an opening. For example, if the notch is circular, this would create a partially circular opening, e.g., a roughly semicircular opening.

The invention also provides a method of automatically opening the sample pan before it is loaded and determining if the pan was truly opened. In a preferred embodiment, a punch element is located above a sample tray and is an integrated part of the autosampler. In order to open the pan, the punch element is pressed against the top cover of the pan. This can be achieved by moving the punch down, or alternatively by moving the autosampler tray up. The punch element has a blunt tip, which presses the center disk portion and partially shears it from the outside section of the cover. During this operation, the punch element does not penetrate the cover and is in contact only with the central disk portion of the cover, which prevents it from touching the sample. The means to determine if the pan is truly opened during the punching process provides the ability to prevent either an unopened or an improperly opened pan from being loaded onto the balance. A force or strain sensor detects the rapid change of the applied force at the beginning of the shearing process. If the cover is not opened properly, the derivative term of the measured signal does not show the expected rapid change and the autosampler does not load the pan. The autosampler then automatically moves to the next sample pan.

Figure 1:
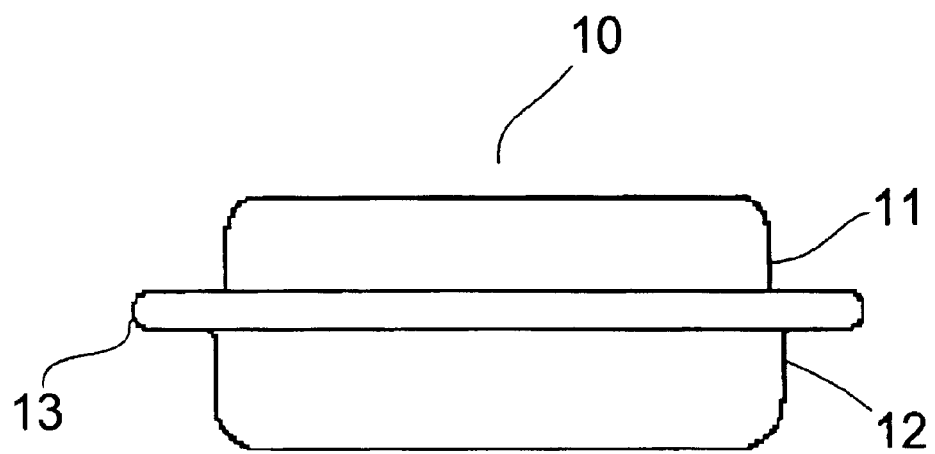
FIG. 1 is a schematic diagram of a side view of a sealed sample pan of an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments of being practiced or being carried out in various ways. Also, it is to be understood that the phraseology and terminology used herein is for the purpose of description and should not be regarded as limiting.

DETAILED DESCRIPTION OF THE INVENTION

Figure 2:
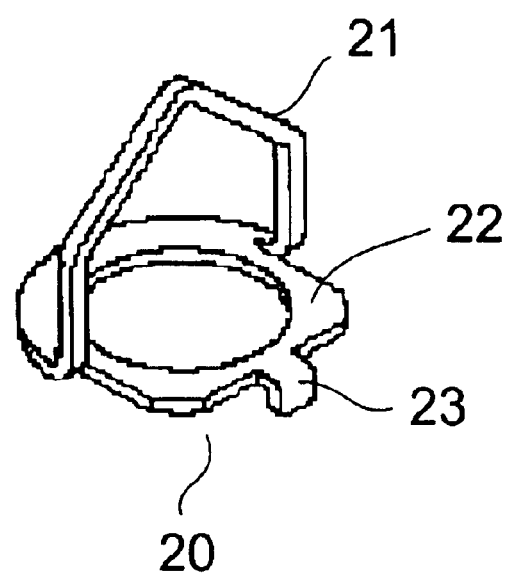
FIG. 2 is a schematic diagram of a bail of an embodiment of the present invention.

FIG. 1 is a schematic diagram of a side view of the sealed sample pan 10 of the present invention. The sealed sample pan 10 is comprised of a pan 12 in which the sample is placed and a cover 11, which is placed on the pan and sealed to it by means of a dedicated pressing tool. The location where the pan 12 and the cover 11 are pressed together is the crimped area 13. Depending on the desired application, the pan 12 and cover 11 can be constructed from various materials including, but not limited to, aluminum, stainless steel, gold, and platinum. Other materials can be used to fabricate the sealed sample pan as long as they are ductile so that they can be sealed and opened and non-reactive, so that they won't gain or lose weight during an experiment. For example, copper would not be suitable, even though it is ductile, because it oxidizes readily and thus would gain weight when heated. FIG. 2 is a schematic diagram of bail 20, which is designed to hold the sealed sample pan and to provide the interface to the TGA balance hang-down hook. Bail 20 can be constructed of formed wired or sheet metal, or can be fabricated in other ways. Depending on the desired application, bail 20 can be constructed from various materials including, but not limited to aluminum, stainless steel, gold, and platinum. Bail 20 includes hook 21, sample pan rim support 22, and orientation tang 23. The most common application is to use aluminum for both parts of the sealed sample pan and the bail. Both the sealed sample pan 10 and bail 20 are designed to be used with an autosampler mounted on a TGA.

Figure 3:
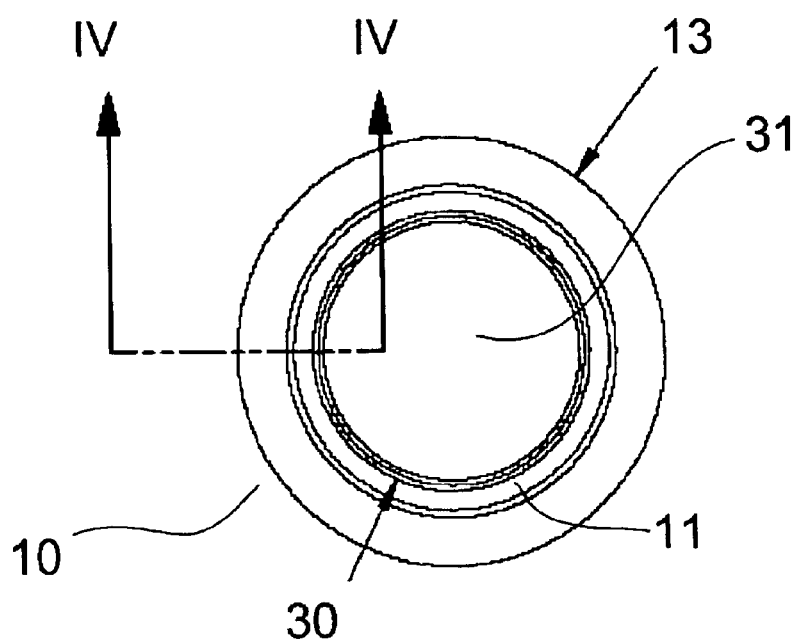
FIG. 3 is a schematic diagram of a top view of a sealed sample pan of an embodiment of the present invention.
Figure 4:
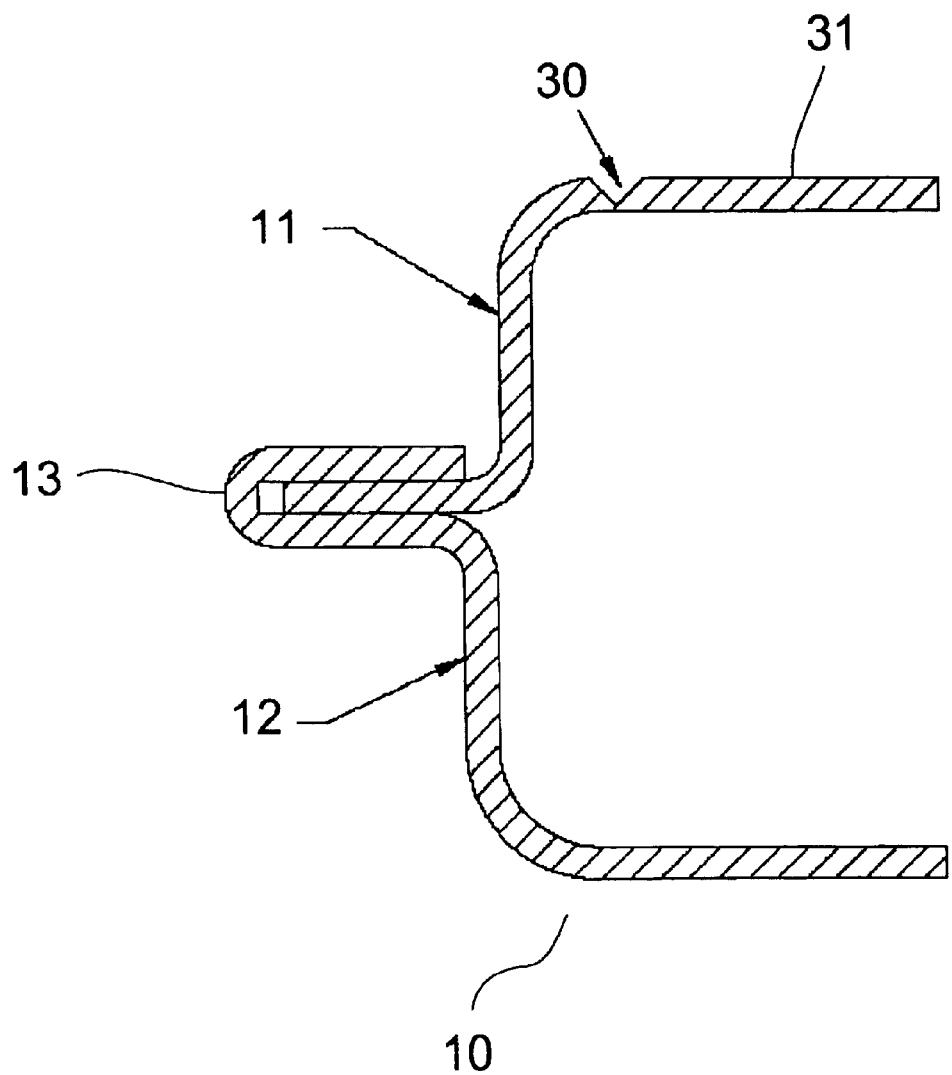
FIG. 4 is a schematic diagram of a cross-sectional view of a portion of a sealed sample pan of an embodiment of the present invention.

FIG. 3 is a schematic diagram of a top view of an exemplary sealed sample pan 10 of the present invention. The sealed sample pan 10, with crimped area 13, provides a means to open a section of the pan cover 11 and expose the sample to the environment just before loading. In this example, a circularly shaped notch 30 is formed on the top flat surface of the pan cover 11. A notch may alternatively be formed on the bottom surface of the pan cover 11. The area inside this circularly shaped notch 30 is the center disk portion 31 of the cover 11. FIG. 4 is a schematic diagram of a cross-sectional view of an exemplary sealed sample pan 10 of the present invention. The sealed sample pan cover 111 and pan 12 are shown in this diagram. The cover 11 and pan 12 are pressed together in the crimped area 13. The diagram also shows how the cover 11 thickness is locally reduced in the circularly shaped notch 30. The cover 11 can be opened by applying a concentrated force to the inside of the circular notch 30, which is the weakest section of the cover, causing part of the center disk portion 31 of the cover 11 to be sheared downward. As a result, part of the center disk portion 31 of the cover 11 is detached from the pan cover and part remains attached, creating, for example, a partially circular opening.

Figure 5:
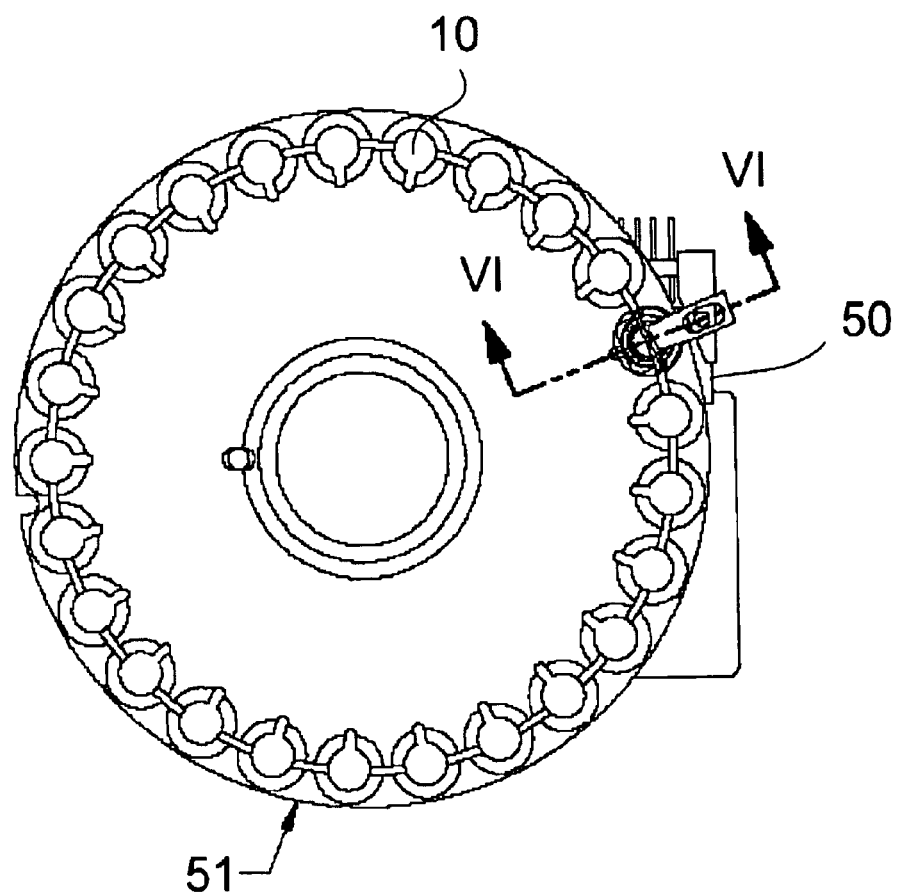
FIG. 5 is a schematic diagram of a top view of a portion of an autosampler of an embodiment of the present invention. This is only a part of the autosampler. It only shows the sample tray and the punch.
Figure 6:
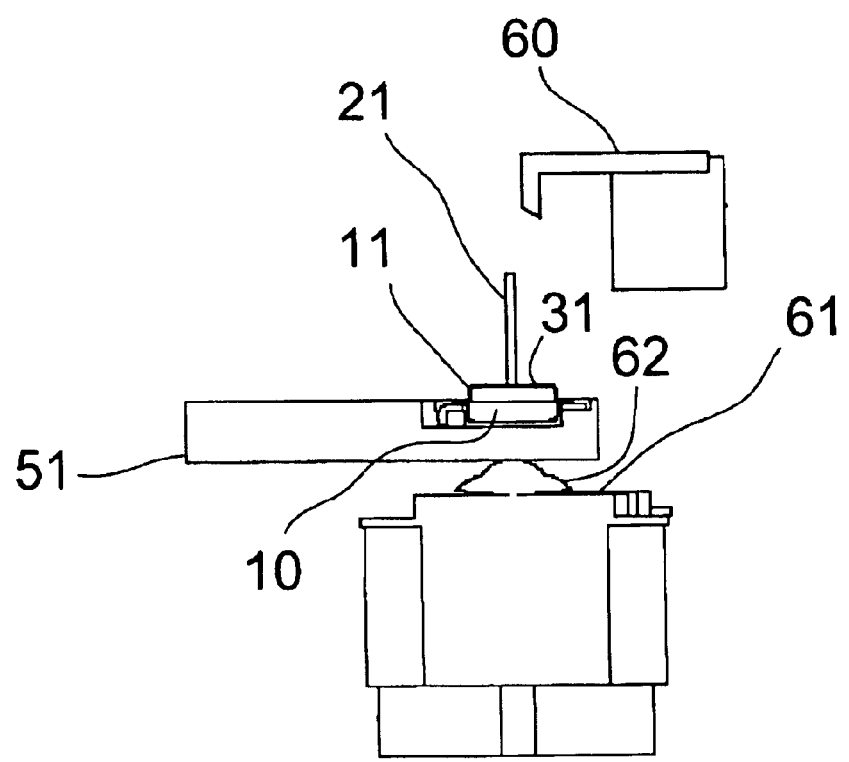
FIG. 6 is a schematic diagram of a cross-sectional view of a portion of an autosampler showing a punch, sealed sample pan, bail, autosampler tray, and force sensor of an embodiment of the present invention.

FIG. 5 is a schematic diagram of a top view of a portion of the autosampler 50 of the present invention. The autosampler tray 51 holds the sealed sample pans 10. FIG. 6 is a schematic diagram of a cross-sectional view of a portion of an autosampler showing a punch element 60, sealed sample pan 10, bail hook 21, autosampler tray 51, force or strain sensor 61 of the present invention, and bearing surface or force coupler 62. Element 62 has two functions; it provides a bearing surface for the sample tray to slide over when the tray rotates, and it couples the force of the punch, which is transferred through the sample pan and sample tray down to the force sensor. The punch element 60 is located above the sample tray 51 and is an integrated part of the autosampler. In order to open the sealed sample pan 10, the punch element 60 is pressed against the top cover 11 of the sealed sample pan 10. This can be achieved alternatively by moving the punch element down, or by moving the autosampler tray up. The punch element 60 has a blunt tip, which presses the center disk portion 31 of the cover 11 and partially shears it from the outside section of the cover 11. During this operation, the punch element 60 does not penetrate the cover and is in contact only with the central disk portion 31 of the cover 11, which prevents it from touching the sample. The means to determine if the pan is truly opened during the punching process provides the ability to prevent an unopened pan from being loaded onto the balance. A force sensor or strain sensor 61 can be used to detect the rapid change of the applied force at the beginning of the shearing process. An exemplary force sensor is the miniature load cell model LBS from Interface, Inc. If the cover 11 is not opened, the derivative term of the measured force or strain signal will not show the expected rapid change and the autosampler will not load the pan and will automatically move to the next sample pan.

Figure 7:
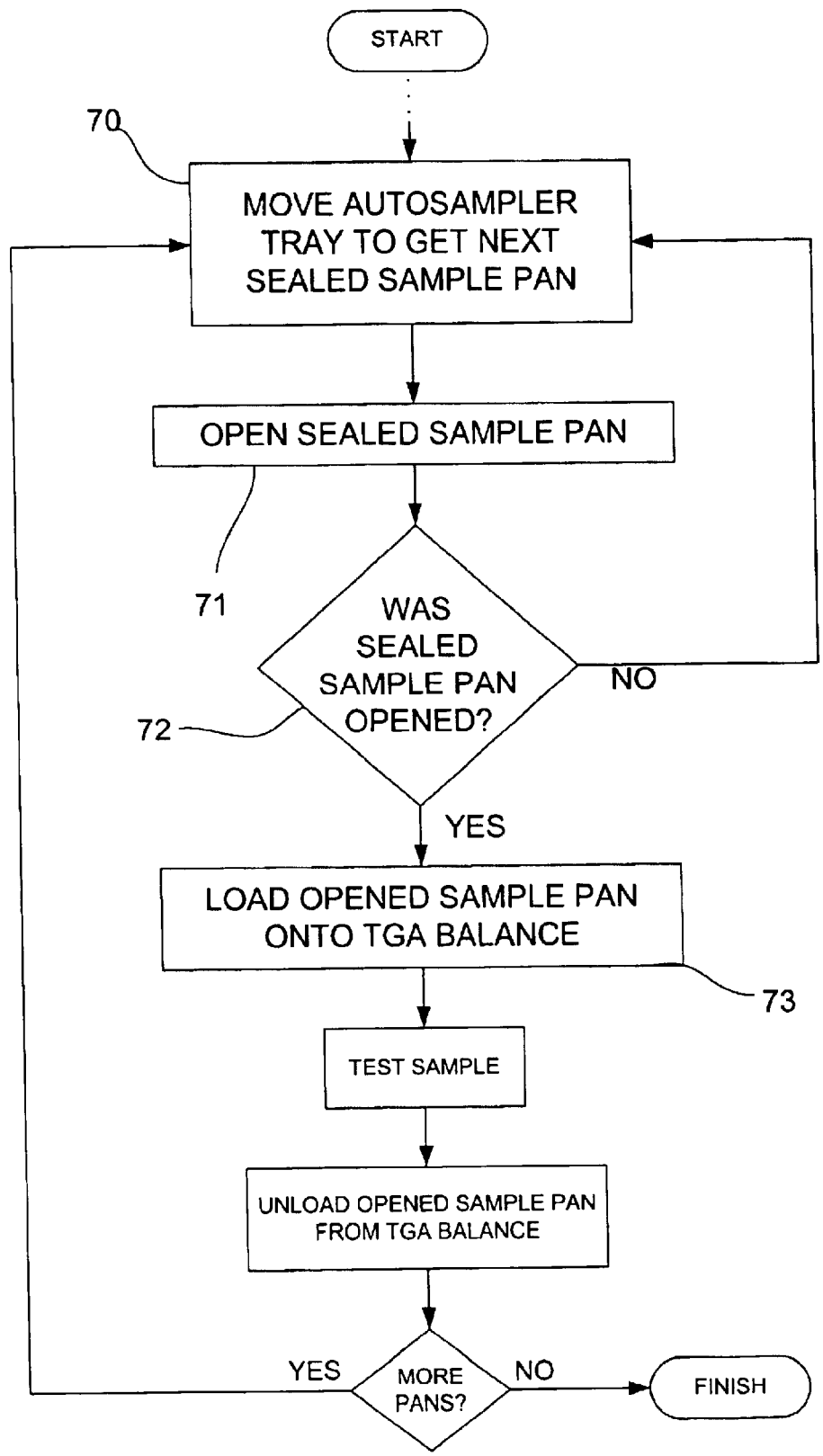
FIG. 7 is a portion of a TGA analysis flowchart showing an exemplary method of automatically moving to the next sealed sample on the autosampler, opening a sealed sample pan, determining if a sealed sample pan was opened, and alternatively loading an opened sealed sample pan onto the TGA balance of an embodiment of the present invention, or moving to the next sealed sample pan if the sealed sample pan was unopened.

FIG. 7 is a portion of an exemplary TGA analysis flowchart showing a typical method of automatically moving to the next sealed sample on the autosampler 70, opening a sealed sample pan 71, determining if a sealed sample pan was opened 72, and alternatively loading an opened sealed sample pan onto TGA balance 73 of the present invention, or moving to the next sealed sample pan if the sealed sample pan was unopened 70.

Figure 8:
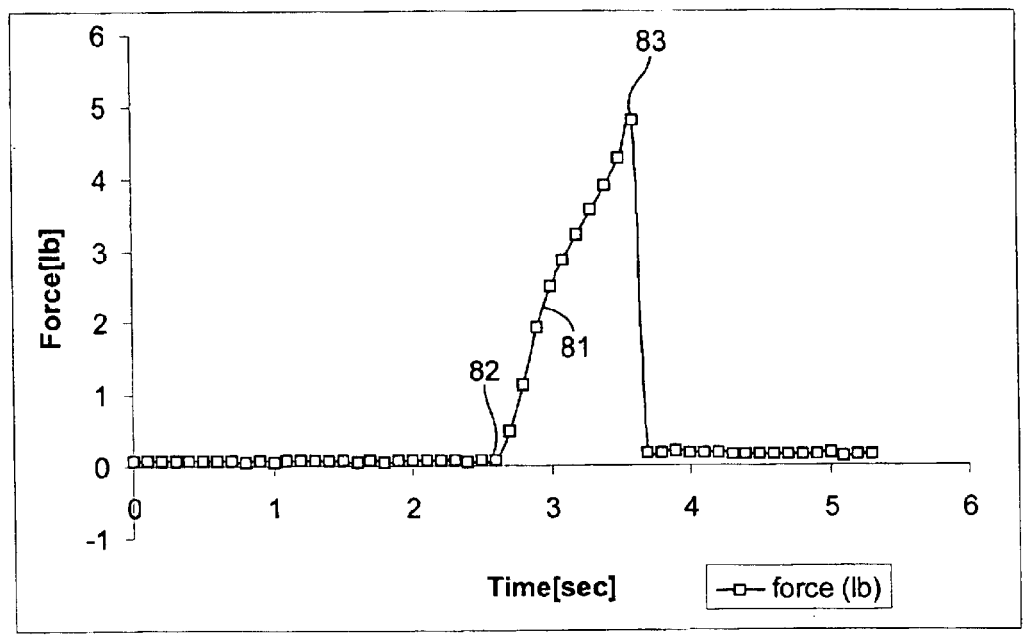
FIG. 8 is a plot of force data collected from an embodiment of the present invention when a pan is opened.
Figure 9:
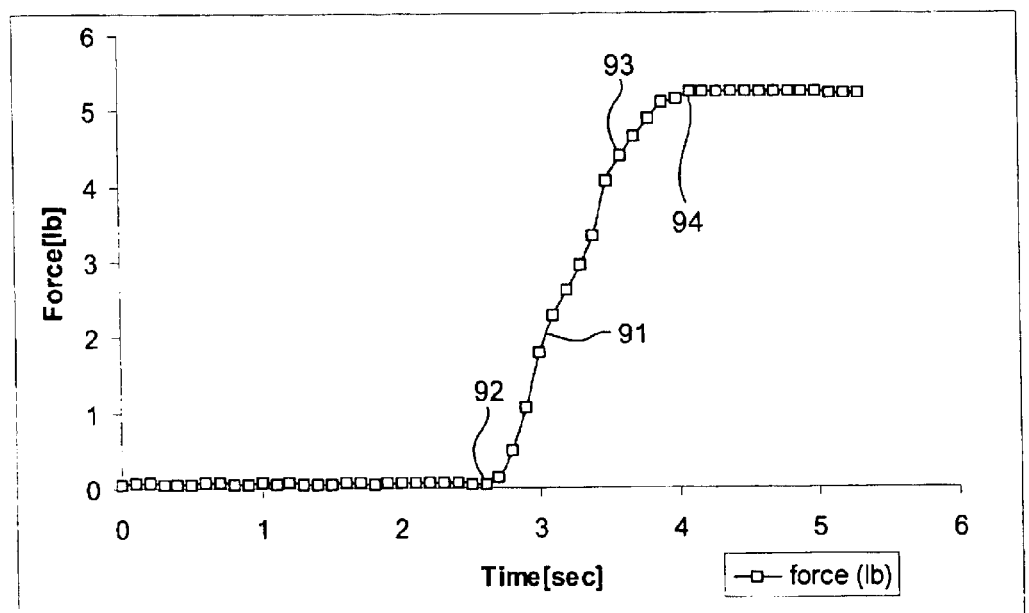
FIG. 9 is a plot of force data collected from an embodiment of the present invention when a pan is not opened.

FIG. 8 is a plot of force data 81 collected from an embodiment of the present invention when a pan is opened. This plot shows the amount of force applied to a sealed sample pan and measured by a force or strain sensor over time. At just after time 2.6 seconds (82) a force of increasing magnitude is applied to center disk portion of the sealed sample pan lid by a punch element. Just after time 3.6 seconds (83) the amount of force measured drops precipitously. This precipitous drop is the rapid change of the measured applied force indicating the beginning of the shearing process. In contrast, FIG. 9 is a plot of force data 91 collected from an embodiment of the present invention when a pan is not opened. This plot also shows the amount of force applied to a sealed sample pan and measured by a force or strain sensor over time. At just after time 2.6 seconds (92) a force of increasing magnitude is applied to center disk portion of the sealed sample pan lid by a punch element. After time 3.6 seconds (93), however, the amount of force measured continues to increase until time 4.1 seconds (94). After time 4.1 seconds (94), the force measure changes very little. There is, therefore, no rapid change in the measured applied force indicating that the sealed sample pan was not opened.

Figure 10:
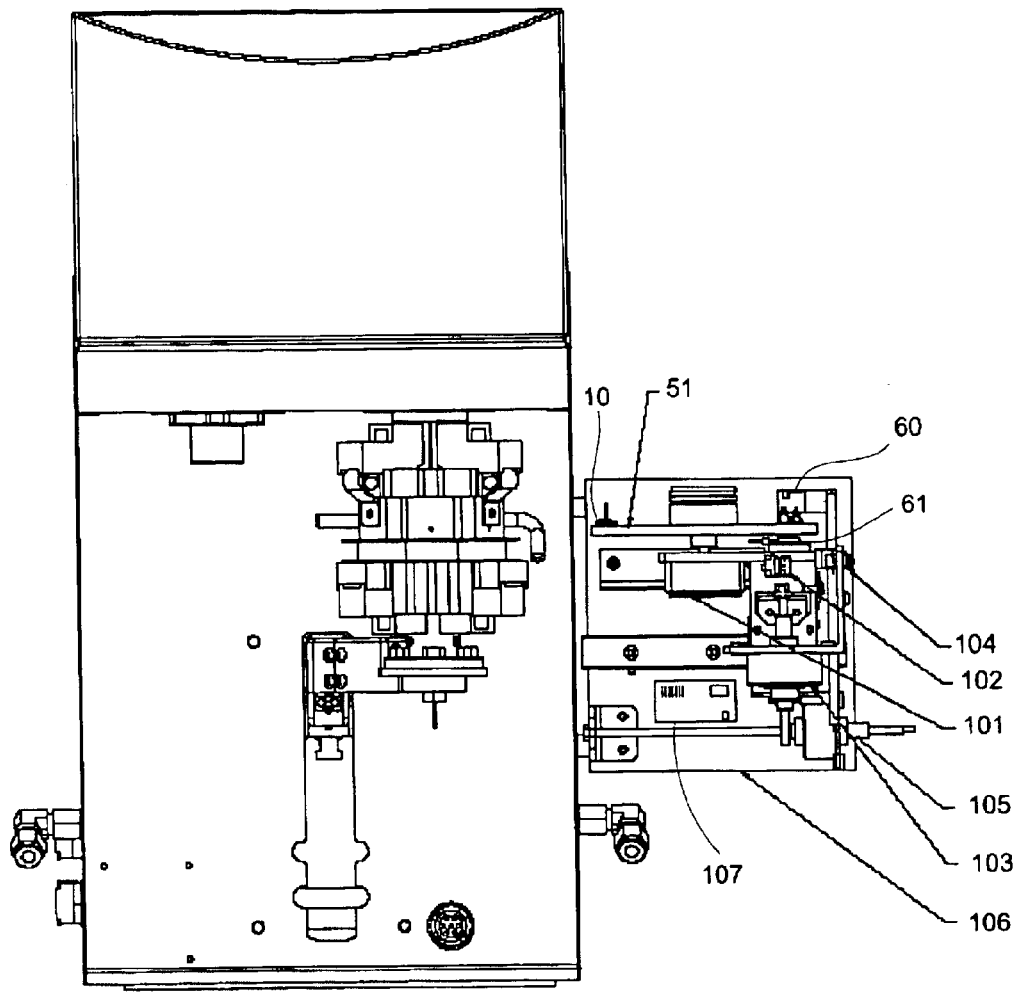
FIG. 10 is a schematic diagram of an autosampler attached to a TGA in the retracted position containing an embodiment of the present invention.
Figure 11:
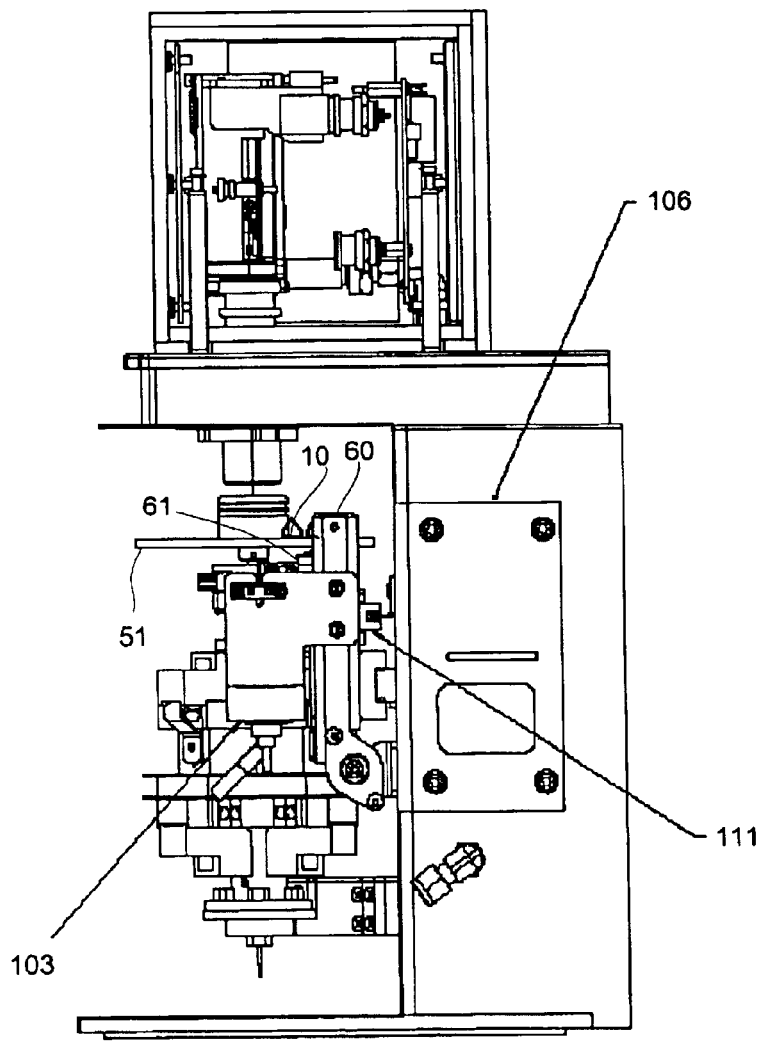
FIG. 11 is a schematic diagram of an autosampler attached to a TGA in the engaged position containing an embodiment of the present invention.

FIG. 10 is a schematic diagram of an autosampler attached to a TGA in the retracted position containing an embodiment of the present invention. The autosampler comprises a sample tray 51, a tray rotation motor 101, a tray rotation sensor 102, a tray lift motor 103, a tray lift sensor 104, a tray translation motor 105, a housing 106 for the entire autosampler, and an electronic control unit 107. FIG. 11 is a schematic diagram of an autosampler attached to a TGA in the engaged position containing an embodiment of the present invention. In addition to a tray lift motor 103 and an autosampler housing 106, the diagram shows a tray translation sensor 111. Both FIG. 10 and FIG. 11 show a punch element 60, sealed sample pan 10, autosampler tray 51, and force or strain sensor 61 of an embodiment of the present invention.

Figure 12:
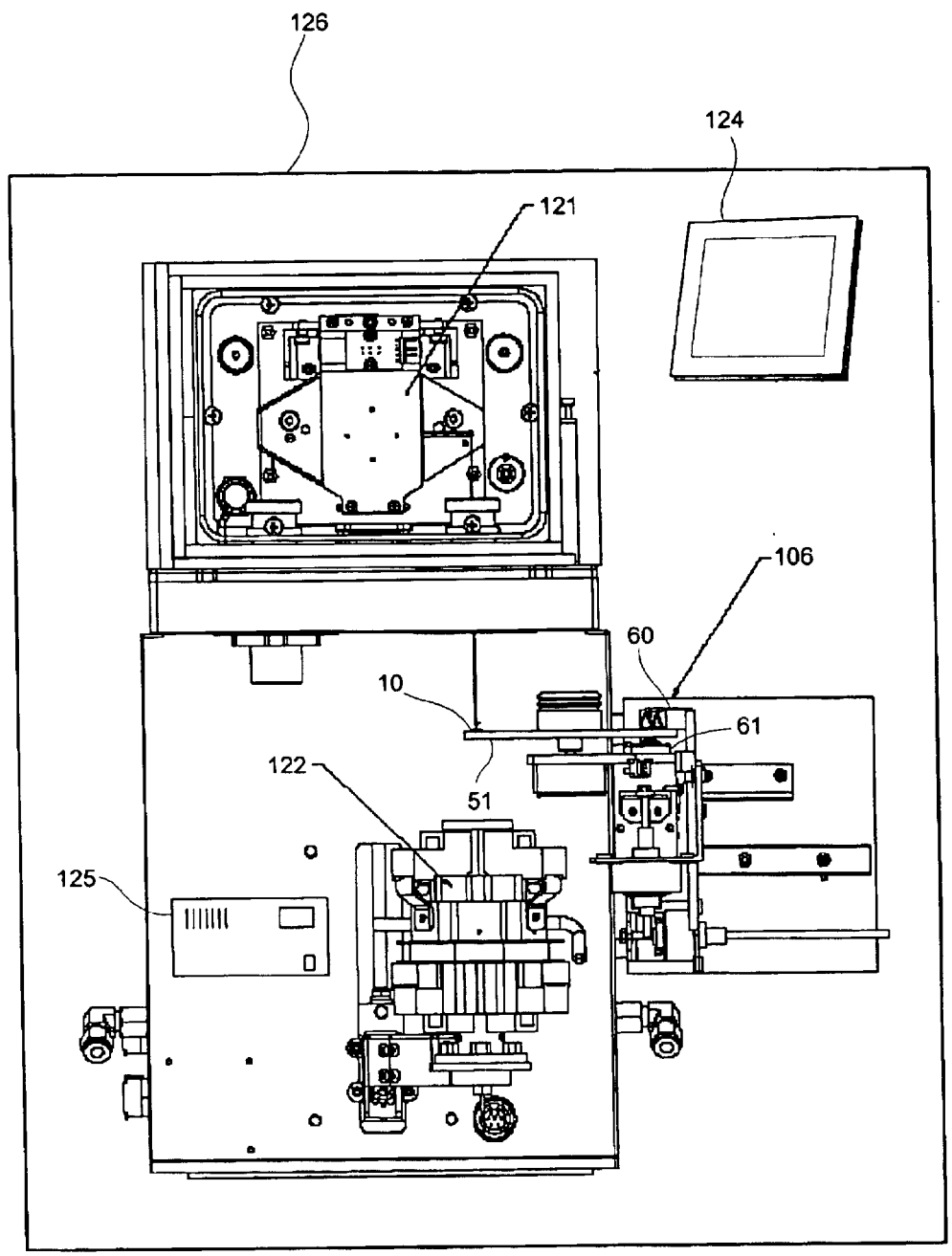
FIG. 12 is a schematic diagram of a TGA containing an embodiment of the present invention.

FIG. 12 is a schematic diagram of a TGA containing an embodiment of the present invention. The TGA comprises a balance 121, a furnace 122, an autosampler enclosed in an autosampler housing 106, a user interface 124, an electronic control unit 125, and a cabinet 126. A punch element 60, sealed sample pan 10, autosampler tray 51, and force or strain sensor 61 of an embodiment of the present invention are attached to the TGA via the autosampler enclosed in autosampler housing 106.

The apparatus, systems, and methods in accordance with an embodiment of the present invention disclosed herein can advantageously improve sample exposure to the ambient environment before TGA testing. The present invention minimizes the probability of the punching element touching the sample and contaminating it or the next sample. It provides an opening in the sealed sample pan cover that is sufficiently large such that the variation in the size of the opening will not affect test results or the repeatability of the results. Finally, it prevents unopened sealed sample pans from being loaded into the TGA balance.

Embodiments of an apparatus, system, and method for opening a TGA autosampler sealed sample pan prior to testing have been described. In the foregoing description, for purposes of explanation, numerous specific details are set forth to provide a thorough understanding of the present invention. It will be appreciated, however, by one skilled in the art that the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the present invention.

In the foregoing detailed description, apparatus, systems, and methods in accordance with embodiments of the present invention have been described with reference to specific exemplary embodiments. Accordingly, the present specification and figures are to be regarded as illustrative rather than restrictive. The scope of the invention is to be defined by the claims appended hereto, and by their equivalents.

What is claimed is:

1. A system for automatically opening a sealed sample pan used in a thermogravimetrical analyzer autosampler comprising:
    (a) a sealed sample pan whose flat cover contains a notch of locally reduced thickness;
    (b) an autosampler, including an autosampler tray on which said pan is placed;
    (c) a punch element;
    (d) a means for pressing the punch element against the cover of the sealed sample pan; and
    (e) a means for detecting the rapid change of an applied force applied by the punch to the cover.

2. The system for automatically opening a sealed sample pan used in a thermogravimetrical analyzer autosampler of claim 1, wherein the notch is formed on the top of the flat part of the cover.

3. The system for automatically opening a sealed sample pan used in a thermogravimetrical analyzer autosampler of claim 1, wherein the notch is formed on the bottom of the flat part of the cover.

4. The system for automatically opening a sealed sample pan used in a thermogravimetrical analyzer autosampler of claim 1, wherein the means for detecting the rapid change of an applied force is a force sensor.

5. The system for automatically opening a sealed sample pan used in a thermogravimetrical analyzer autosampler of claim 1, wherein the means for detecting the rapid change of an applied force is a strain sensor.

6. The system for automatically opening a sealed sample pan used in a thermogravimetrical analyzer autosampler of claim 1, wherein the means for pressing the punch element against the cover of the sealed sample pan is moving the punch element down.

7. The system for automatically opening a sealed sample pan used in a thermogravimetrical analyzer autosampler of claim 1, wherein the means for pressing the punch element against the cover of the sealed sample pan is moving the autosampler tray up.

8. The system for automatically opening a sealed sample pan used in a thermogravimetrical analyzer autosampler of claim 1, further comprising a bail to hold the sealed sample pan and to provide an interface to the thermogravimetrical analyzer balance hang-down hook.

9. The system for automatically opening a sealed sample pan used in a thermogravimetrical analyzer autosampler of claim 1, wherein the notch is shaped in the form of a circle.

10. The system for automatically opening a sealed sample pan used in a thermogravimetrical analyzer autosampler of claim 1, wherein the notch shaped in the form of a polygon.

11. The system for automatically opening a sealed sample pan used in a thermogravimetrical analyzer autosampler of claim 1, wherein the notch is shaped in the form of an oval.

12. The system for automatically opening a sealed sample pan used in a thermogravimetrical analyzer autosampler of claim 1, wherein the notch is shaped in the form of a teardrop.

13. A method for automatically opening and loading a sealed sample pan used in a thermogravimetrical analyzer autosampler comprising:
   (a) opening the sealed sample pan by providing the sealed sample pan, having a cover, with a notch defining a central disk portion of the cover and applying a concentrated force to the central disk portion of the cover;
   (b) determining if an opening was made; loading the sealed sample pan if the opening was made; and
   (c) moving to the next sample pan if the opening was not made.

14. The method of claim 13, wherein the notch defining the central disk portion of the cover is provided by reducing locally the thickness of the top flat surface of the cover.

15. The method of claim 13, wherein the notch defining the central disk portion of the cover is provided by reducing locally the thickness of the bottom flat surface of the cover.

16. The method of claim 13, wherein the concentrated forced is applied by pressing a punch element against the central disk portion of the cover.

17. The method of claim 16, wherein the punch element is pressed against the central disk portion of the cover by moving the punch element down.

18. The method of claim 16, wherein the punch element is pressed against the central disk portion of the cover by moving an autosampler tray up to the punch element.

19. The method of claim 13, wherein determining if an opening was made is determined by detecting a rapid change of the applied concentrated force.

20. The method of claim 19, wherein the rapid change of the applied concentrated force is detected using a force sensor.

21. The method of claim 19, wherein the rapid change of the applied concentrated force is detected using a strain sensor.

22. The method of claim 13, wherein the notch defining the central disk portion is shaped in the form of a circle.

23. The method of claim 13, wherein the notch defining the central disk portion is shaped in the form of a polygon.

24. The method of claim 13, wherein the notch defining the central disk portion is shaped in the form of a oval.

25. The method of claim 13, wherein the notch defining the central disk portion is shaped in the form of a teardrop.

26. An autosampler comprising:
   (a) a sample tray;
   (b) a tray rotation motor;
   (c) a tray rotation sensor;
   (d) a tray lift motor;
   (e) a tray lift sensor;
   (f) a tray translation motor;
   (g) a tray translation sensor;
   (h) an autosampler electronic control unit;
   (i) an autosampler housing;
   (j) a sealed sample pan whose flat cover contains a notch of locally reduced thickness;
   (k) a punch element;
   (l) a means for pressing the punch element against the cover of the sealed sample pan; and
   (m) a means for detecting the rapid change of an applied force applied by the punch to the cover.

27. A thermogravimetrical analyzer comprising:
   (a) a balance;
   (b) a furnace;
   (c) a thermogravimetrical analyzer electronic control unit;
   (d) a thermogravimetrical analyzer user interface;
   (e) a thermogravimetrical analyzer cabinet;
   (f) a sealed sample pan whose flat cover contains a notch of locally reduced thickness;
   (g) an autosampler, including an autosampler tray on which said pan is placed;
   (h) a punch element;
   (i) a means for pressing the punch element against the cover of the sealed sample pan; and
   (j) a means for detecting the rapid change of an applied force applied by the punch to the cover.

* * * * *